United States Patent
Berger et al.

[11] Patent Number: 5,925,325
[45] Date of Patent: Jul. 20, 1999

[54] PLASMA UNIT

[75] Inventors: Steffen Berger, Düsseldorf; Johannes Messelhäuser, Tübingen; Walter Schönherr, Hennef/Sieg, all of Germany

[73] Assignee: Arplas Gesellschaft Für Plasmatechnologie mbH, Weissandt-Golzau, Germany

[21] Appl. No.: 08/836,917

[22] PCT Filed: Nov. 23, 1995

[86] PCT No.: PCT/EP95/04619

§ 371 Date: May 23, 1997

§ 102(e) Date: May 23, 1997

[87] PCT Pub. No.: WO96/15851

PCT Pub. Date: May 30, 1996

[30] Foreign Application Priority Data

Nov. 24, 1994 [DE] Germany .............................. 44 43 240

[51] Int. Cl.⁶ .............................. B01J 15/00; B01J 19/12
[52] U.S. Cl. ...................................................... 422/186.05
[58] Field of Search ........................................ 422/186.05

[56] References Cited

U.S. PATENT DOCUMENTS

| | | | |
|---|---|---|---|
| 2,167,718 | 8/1939 | Harris, Jr. et al. ........................ | 204/31 |
| 4,298,440 | 11/1981 | Hood ........................................ | 204/165 |
| 5,079,033 | 1/1992 | Schulz et al. ............................. | 427/44 |
| 5,190,703 | 3/1993 | Rose et al. ................................ | 264/22 |
| 5,234,723 | 8/1993 | Babacz .................................... | 427/491 |
| 5,316,739 | 5/1994 | Yoshikawa et al. ............... | 422/186.05 |
| 5,558,843 | 9/1996 | Glocker et al. ..................... | 422/186.05 |

FOREIGN PATENT DOCUMENTS

| | | |
|---|---|---|
| 0 039 517A1 | 11/1981 | European Pat. Off. . |
| 0 437 267A1 | 7/1991 | European Pat. Off. . |
| 41 41 895 A1 | 6/1993 | Germany . |
| 61-069804 | 4/1986 | Japan . |
| 61-108605 | 5/1986 | Japan . |
| 2198626 | 8/1990 | Japan . |
| WO 94/03263 | 2/1994 | WIPO . |

*Primary Examiner*—Daniel J. Jenkins
*Attorney, Agent, or Firm*—Finnegan, Henderson, Farabow, Garrett & Dunner, L.L.P.

[57] ABSTRACT

The invention relates to a plasma unit, in particular for treating solids containing alkyl groups with a low-temperature plasma, having a treatment reactor and plasma-generation apparatuses assigned to the treatment reactor. It is provided that an apparatus (14) for generating a melt of the solids (24) to be treated is assigned to the treatment reactor (12).

15 Claims, 1 Drawing Sheet

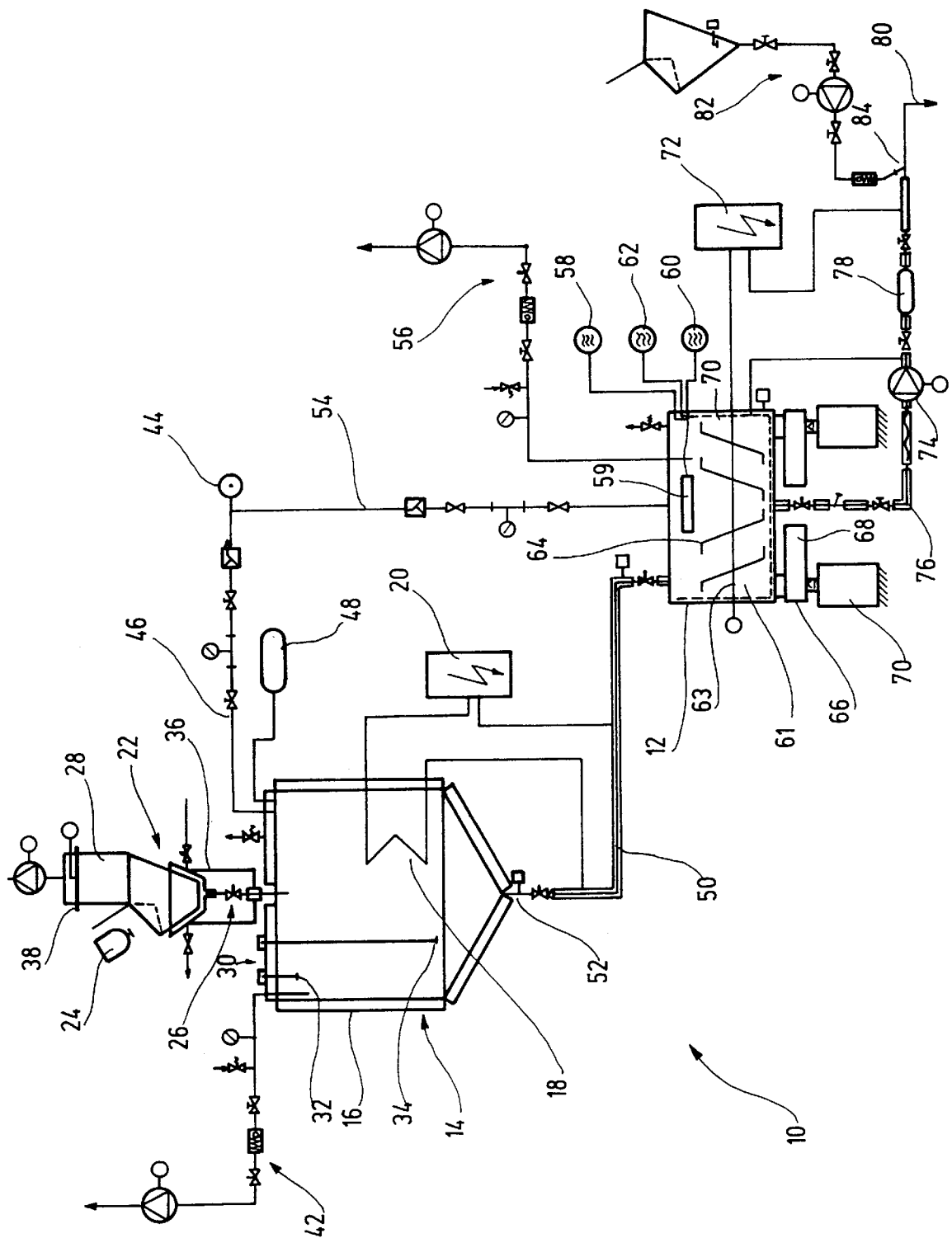

PLASMA UNIT

The invention relates to a plasma unit, in particular for treating solids containing alkyl groups with a low-temperature plasma, having a treatment reactor and plasma-generation apparatuses assigned to the treatment reactor.

Plasma units of this type are known. Thus, plasma units of different types of construction are known which have a treatment reactor and plasma-generation apparatuses assigned to the treatment reactor. The treatment reactor possesses a suitable closable orifice through which the objects to be treated can be introduced into the treatment reactor. Thus, for example, DE 41 41 805 A1 discloses a device for producing thermoplastic components using low-temperature plasmas which has a vacuum chamber connected to a vacuum pump. A thermoplastic in granule form can be introduced into the vacuum chamber via a chamber door for the low-temperature plasma treatment. In addition, it is known to introduce solids containing alkyl groups, for example polyolefins, in the form of powder, fibers, films or entire shaped components, into treatment reactors of this type, in order to achieve a surface treatment by means of the low-temperature plasma.

It is a disadvantage of all known plasma units that they are unsuitable for ensuring a penetrating, long-term stable modification of the solids containing alkyl groups to be treated.

The object underlying the invention was therefore to create a plasma unit of the generic type which is of a simple structure and by means of which a homogeneous chemical modification, that is a chemical modification extending over the entire spatial extent of the solid to be treated, is possible.

According to the invention, the object is achieved by a plasm unit having the features specified in claim 1. By means of the fact that an apparatus for generating a melt of the solids to be treated is assigned to the treatment reactor, it is possible in a simple manner to convert the solids into a melt prior to and/or during the low-temperature plasma treatment. It has surprisingly been found that solids converted into a melt, in particular solids containing alkyl groups, can be specifically subjected to a qualitatively and quantitatively high-grade chemical modification. In particular, a chemical modification becomes possible which far surpasses a mere surface treatment of the solids containing alkyl groups.

In an advantageous development of the invention, it is provided that the treatment reactor and the apparatus for generating the melt form separate modules of the plasma unit which are linked to one another. By this means it advantageously becomes possible to optimize each of the modules for its intended purpose, so that overall a variable adaptable plasma unit is created.

In a further advantageous development of the invention, it is provided that the treatment reactor has means for agitating the melt during the plasma treatment. By this means it becomes possible to achieve a homogeneous mixing or homogeneous treatment of the solids containing alkyl groups, which have been converted into the melt, by the low-temperature plasma, so that an essentially complete uniform chemical modification is achieved.

Further advantageous developments of the invention are given by the remaining features specified in the subclaims.

The invention is described in more detail below in an illustrative example with reference to the associated drawing, which shows a plasma unit diagrammatically.

The FIGURE shows a plasma unit designated generally by 10. For reasons of clarity, components which are not essential for the invention, such as mechanical joints, mechanical attachments, detailed depictions of housings etc., have been dispensed with on the diagram. In addition, the plasma unit according to the invention is not restricted to the chosen spatial representation. Thus, any other other assignment of the individual components of the plasma unit, which are still to be described below, can be selected, if they, in their interaction, ensure the desired treatment of the solids containing alkyl groups.

Principal components of the plasma unit 10 are a treatment reactor 12 and an apparatus 14 for generating a melt. The apparatus 14 essentially comprises a container 16, to which is assigned a heating apparatus 18. The heating apparatus 18 can be, for example, pipes which protrude into the container 16 and through which flows a heating medium, for example a thermal oil. Assigned to the heating apparatus 18 is a heating and controlling apparatus 20 which controls heating of the heating circuit as a function of the particular thermal regime for the particular solid to be treated.

The container 16 has a filler arrangement 22, by means of which the container 16 can be charged with the solids containing alkyl groups 24 which are merely indicated here. A metering apparatus 26 and a dedusting apparatus 28 are assigned to the filler arrangement 22. The metering apparatus 26 permits a defined delivery, for example of a certain mass or of a certain volume of the solid 24 per unit time into the container 16. The container 16 possesses a filling level indicator 30, which has, for example, a first filling level probe 32 for a maximum filling level and a second filling level probe 34 for a minimum filling level. Between the container 16 and the filler arrangement 22, a cooling apparatus 36 can be arranged which prevents heating of the solid 24 already in the filler arrangement 22 due to heat arising in the container 16. For this purpose, pipes and vessels can be provided through which flows a refrigerant, and which are not described in more detail. The dedusting apparatus 28 has a filter 38 and a fan 40.

The container 16 is provided with an evacuation apparatus 42 by means of which a vacuum can be generated in the container 16.

In addition, a source 44, which is merely indicated here, of at least one inert gas and/or at least one reaction gas is assigned to the plasma unit 10. The source 44 is connected to the vessel 16 via a first feed 46. In addition, a gas analyzer 48 is provided, which is coupled to the container 16.

The treatment vessel 12 is connected to the container 16 via a connection line 50. The connection line 50 is heatable, the heating circuit of the connection line 50 preferably being connected to the heating and controlling apparatus 20, so that a shared heating circuit together with the heating apparatus 18 is given.

According to an illustrative example which is not shown here, the container 16 can be mounted with its outlet orifice 52 directly on the treatment reactor 12, so that the length of the connection line 50 is restricted to a minimum.

A second feed 54 connects the treatment reactor 12 to the source 44 of the inert gases or reaction gases. The treatment reactor 12 is likewise connected to an evacuation apparatus 56 for generating a vacuum in the treatment reactor 12. The treatment reactor 12 is provided with plasma generators 58, 60 and 62, which are indicated here. The generators 58 to 62 are arranged in such a manner that a plasma excitation can be performed by these in the treatment reactor 12. For this purpose, for example, at least one electrode 59 arranged in the treatment reactor is connected to a microwave generator 58, to a high-frequency feed 60 and to a further plasma excitation source 62. The specific construction of the electrodes is not to be considered in more detail in the context of the present description. These can be, for example, rod-shaped, spherical, half-shell-shaped, etc. Further types of plasma sources can be assigned to the treatment reactor 12.

An agitator 61 is arranged within the treatment reactor 12. The agitator 61 possesses paddle-shaped mixing tools 64 arranged on a driveable shaft 63, for example. The construction of the agitator 61 shown here is merely an example. Thus, obviously, any other form of a suitable agitator 61 is conceivable by which stirring, mixing, etc., is possible. The structure of the agitator 61 can be adapted to a melt viscosity. The treatment reactor 12 is provided with a weighing apparatus 66 which has weighing cells 68 which rest on one side on a bearing 70 and on the other side support the treatment reactor 12.

A further heating apparatus 70 is assigned to the treatment reactor 12, via which heating apparatus heating of the interior of the treatment reactor 12 is possible. The heating apparatus 70 is connected to a heating and controlling apparatus 72, via which a defined amount of heat can be provided.

The treatment reactor 12 is connected to a transfer line 76 having a feed pump 74. Both the feed pump 74 and the transfer line 76 are incorporated in the heating circuit fed via the heating and controlling apparatus 72. An analyzer and controller 78, for example a so-called MFI-Controller, is incorporated within the transfer line 74 [sic]. The transfer line 76 leads to a manufacturing apparatus 80, which is only indicated diagrammatically here. The manufacturing apparatus 80 can be, for example, an extruder, a granulator, a dispersion apparatus, an injection-molding machine, a shock-cooler, a mixing unit for producing solutions, dispersions, emulsions, compounds and/or blends, an impregnation device, a spraying or injection device and/or a device for producing composites. Upstream of the manufacturing apparatus 80, a feed device 82 is provided which opens out in the transfer line 76 at a mixing point 84.

The connection line 50 and/or the transfer line 76 can have, for example in the production and treatment of polyolefin melts, conveyor screws or extruder screws.

Metering, actuating and drive elements whose functions are generally known and which are not described in more detail are assigned to the individual assemblies of the plasma unit 10.

The plasma unit 10 shown in the FIGURE performs the following function:

A solid containing alkyl groups 24 is charged into the container 16 of the apparatus 14 via the filler arrangement 22. This solid can be, for example, polyolefins or waxes. If appropriate, different solids containing alkyl groups can be premixed with one another within the filler arrangement 22. The amount of solids 24 to be introduced can be selected using the metering apparatus 26 and/or the filling level indicator 30. As will be inferred from the explanation below, the container 16 can be continuously replenished with solids 24. Within the container 16, the charged solids 24 are heated by means of the heating apparatus 18 above their melting point, so that a melt of the solids 24 is formed. During the generation of the melt, the container 16 can be degassed via the evacuation apparatus 42. The melt situated in the container 16 thus remains under a vacuum. An inert gas, for example helium and/or argon, can be charged into the container 16 via the feed 46. The gas state present in the container 16 is monitored via the gas analyzer 48. After generating the melt, this is transferred into the treatment reactor 12 via the connection line 50. The connection line 50 is heated, so that solidification of the melt during the transfer is prevented. The treatment reactor 12 is likewise heatable via the heating apparatus 70, so that the melt state can also be maintained there. Agitation or mixing of the charged melt is performed by means of the agitator 61.

A vacuum is generated in the treatment reactor 12 via the evacuation apparatus 56. An inert gas and/or reaction gas is charged via the feed 54, in accordance with the desired low-temperature plasma treatment of the melt. In accordance with the chosen starting material, a varying sequence of specific combinations of the process gases can be established, that is a first treatment with an inert gas plasma, preferably with helium and/or argon, a subsequent treatment with a reaction gas plasma, preferably with oxygen and/or nitrogen, or else treatment with a plasma which is generated from a mixture of the abovementioned gases. A low-temperature plasma is excited via the plasma generators 58, 60 and 62. In accordance with the selected starting materials and/or the desired treatment effect, a sequence of different plasma excitation states can be set in this case. Thus, the treatment can be performed either via one of the plasma generators 60 to 62, a sequential treatment via at least two of the plasma generators 58, 60 and 62 and/or a combined treatment with alternately selected plasma generators 58, 60 and 62, with, for example, two of the generators also being able to contribute simultaneously to the plasma generation. In accordance with the coupling of the electrodes 59 to a microwave generator, a high-frequency feed or another plasma excitation source, sequences of different low-temperature plasmas can be generated in the treatment reactor 12. In accordance with the selected feed of the inert gas, the reaction gas or the reaction gas mixture via the feed 54, the process parameters in the treatment reactor 12 can be set variably. The setting of the process parameters is directed in this case according to the starting product and the desired application of the end product as well as a chosen geometry of the treatment reactor 12. During the low-temperature plasma treatment, the melt can be kept in motion, continuously or alternatingly, by means of the agitator 10, so that a homogeneous chemical modification can be performed by means of the low-temperature plasma treatment of the entire melt, that is over its entire spatial extent. The treatment is thus performed essentially uniformly. Via the weighing apparatus 66, the inflow of the melt to the treatment reactor 12 can be restricted to a defined rate, so that an optimum treatment is possible.

After completion of the treatment, the chemically modified melt is fed via the transfer line 76 to a manufacturing apparatus 80. By means of the analyzer and controller 78, the result achieved using the treatment can be continuously monitored. Prior to feed of the treated melt to the manufacturing apparatus 80, there is the possibility of adding additives, for example dyes, fillers, reactants, etc., via the feed apparatus 82.

Overall, it is possible by means of the plasma unit 10 according to the invention to achieve an essentially continuous treatment flow of solids containing alkyl groups. For example, while a first batch of a solid 24 which has been previously converted into the melt is being treated in the treatment reactor 12, a second batch of a solid 24 can simultaneously be converted into the melt in the apparatus 14. Once the first batch has been treated and passed onto the manufacturing apparatus 80, the melt generated in the apparatus 14 can be transferred to the treatment reactor 12 and the apparatus 14 can be charged with the next batch of solids 24.

The fundamental structure is intended to be made clear with reference to the flow diagram of the plasma unit 10 shown in the FIGURE. The structure pictured is not binding for the invention, and just represents one possible example. Thus, the modular principal components of the plasma unit 10, namely the treatment reactor 12 and the apparatus 14, can also be combined with one another, in particular in such a manner that generation of the melt is possible within the treatment reactor 12.

We claim:

1. Plasma unit, in particular for treating solids containing alkyl groups with a low-temperature plasma, having a treatment reactor and plasma-generation apparatuses assigned to the treatment reactor, characterized in that an apparatus (14) for generating a melt of the solids (24) to be treated is assigned to the treatment reactor (12).

2. Plasma unit according to claim 1, characterized in that the treatment reactor (12) and the apparatus (14) are modular components of the plasma unit (10) which are coupled together mechanically and/or in terms of the process.

3. Plasma unit according to one of the preceding claims, characterized in that the apparatus (14) has a container (16) which is heatable by means of a heating apparatus (18) for generating the melt.

4. Plasma unit according to one of the preceding claims, characterized in that a vacuum can be generated in the container (16) via an evacuation apparatus (42).

5. Plasma unit according to one of the preceding claims, characterized in that the container (16) is connected via at least one feed (46) to a source (44) of at least one inert gas and/or at least one reaction gas.

6. Plasma unit according to one of the preceding claims, characterized in that the treatment reactor (12) has at least one agitator (61) for agitating the melt before, during and/or after the treatment.

7. Plasma unit according to one of the preceding claims, characterized in that the treatment reactor (12) can be heated via at least one heating apparatus (70).

8. Plasma unit according to one of the preceding claims, characterized in that at least one plasma source (58, 60, 62) for excitation of a plasma is assigned to the treatment reactor (12).

9. Plasma unit according to claim 8, characterized in that the plasma sources (58, 60, 62) are a microwave generator, a high-frequency feed or another suitable plasma source and these can be selected individually, alternately, and/or in combinations.

10. Plasma unit according to one of the preceding claims, characterized in that the treatment reactor (12) is connected to the source (44) via a feed (54).

11. Plasma unit according to one of the preceding claims, characterized in that the treatment reactor (12) is connected to the apparatus (14) via a heatable connection line (50) for transferring the melt.

12. Plasma unit according to one of the preceding claims, characterized in that the apparatus (14) is mounted directly on the treatment reactor (12) or is connected directly to the latter.

13. Plasma unit according to one of the preceding claims, characterized in that the apparatus (14) is integrated into the treatment reactor (12).

14. Plasma unit according to one of the preceding claims, characterized in that a preferably heatable transfer line (76) is arranged downstream of the treatment reactor (12), via which transfer line the treated melt can be fed to a manufacturing apparatus (80).

15. Plasma unit according to one of the preceding claims, characterized in that the transfer line (76) has a mixing point (84), at which the treated melt can be admixed with additives via a feed apparatus (82).

* * * * *